United States Patent [19]

Vecsey

[11] Patent Number: 5,640,874

[45] Date of Patent: Jun. 24, 1997

[54] PROGRESSIVE DIE/CARRIER APPARATUS AND METHOD OF FORMING SURGICAL NEEDLES AND/OR INCISION MEMBERS

[75] Inventor: Russell J. Vecsey, Easton, Conn.

[73] Assignee: United States Surgical Corporation, Norwalk, Conn.

[21] Appl. No.: 458,213

[22] Filed: Jun. 2, 1995

[51] Int. Cl.⁶ .............................. B21G 1/00; B21D 28/10
[52] U.S. Cl. .......................... 72/337; 72/339; 72/404; 163/1; 163/5
[58] Field of Search .................. 72/404, 330, 331, 72/337, 339; 163/5, 1

[56] References Cited

U.S. PATENT DOCUMENTS

| | | | |
|---|---|---|---|
| 3,461,708 | 8/1969 | Pepe | 72/337 |
| 4,455,858 | 6/1984 | Hettich | 163/5 |
| 4,524,815 | 6/1985 | Pavel | 163/5 |
| 4,541,470 | 9/1985 | Pavel | 163/5 |
| 4,598,753 | 7/1986 | Zylbert | 163/5 |
| 4,672,734 | 6/1987 | Kawada et al. | 163/1 |
| 4,785,868 | 11/1988 | Koenig, Jr. | 163/5 |

FOREIGN PATENT DOCUMENTS

| | | | |
|---|---|---|---|
| 0650698 | 3/1995 | European Pat. Off. | |
| 2737648 | 3/1979 | Germany | 163/1 |
| 2947806 | 7/1981 | Germany | 163/1 |
| 147734 | 5/1992 | Japan | 163/1 |

*Primary Examiner*—Daniel C. Crane

[57] ABSTRACT

There is disclosed an apparatus and a method for progressively forming high strength surgical needles from bulk needle stock material. The apparatus generally includes a series of progressive needle processing stations. A first series of needle processing stations removes material from needle stock material to rough form needle blanks attached to a carrier strip while a second series of processing stations refine the rough formed needle blanks attached to the strip into the desired surgical needles. The disclosed method generally includes the steps of gutting needle stock material to rough form needle blanks attached to a carrier strip and progressively coining the rough formed blanks into surgical needles. Finally, there is disclosed a high bend strength surgical needle formed on the disclosed apparatus or by the disclosed method. Preferably, the surgical needle is a surgical incision member having a predetermined radius of curvature and an optimized conical radius at the tips.

24 Claims, 13 Drawing Sheets

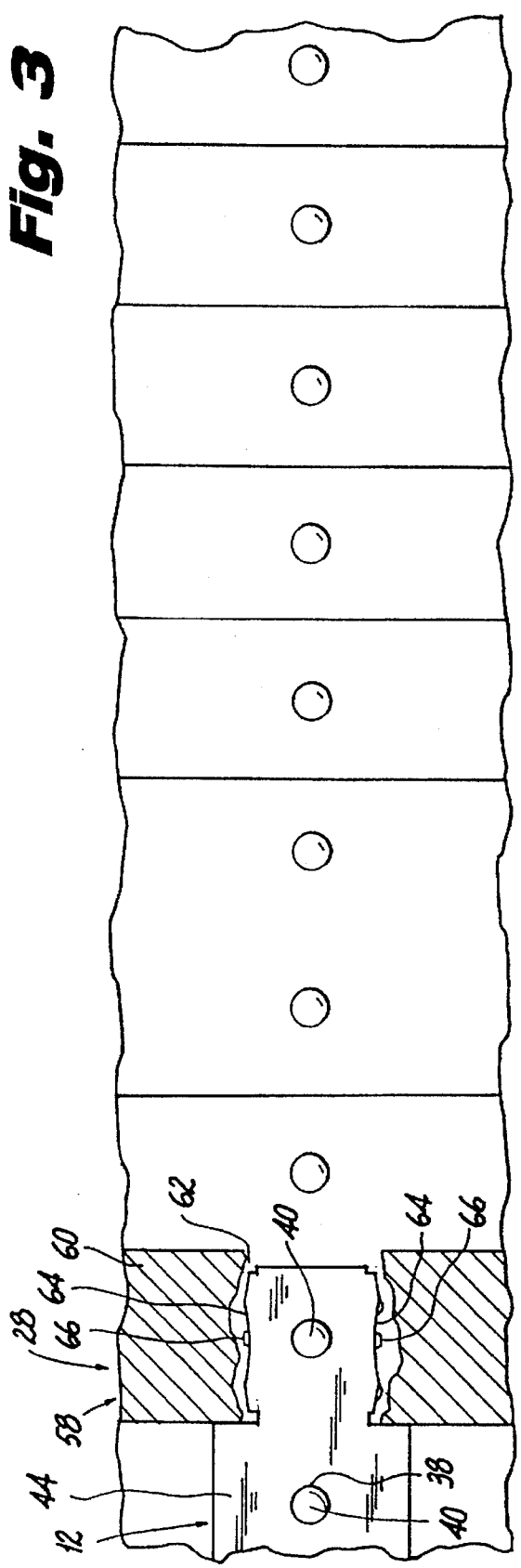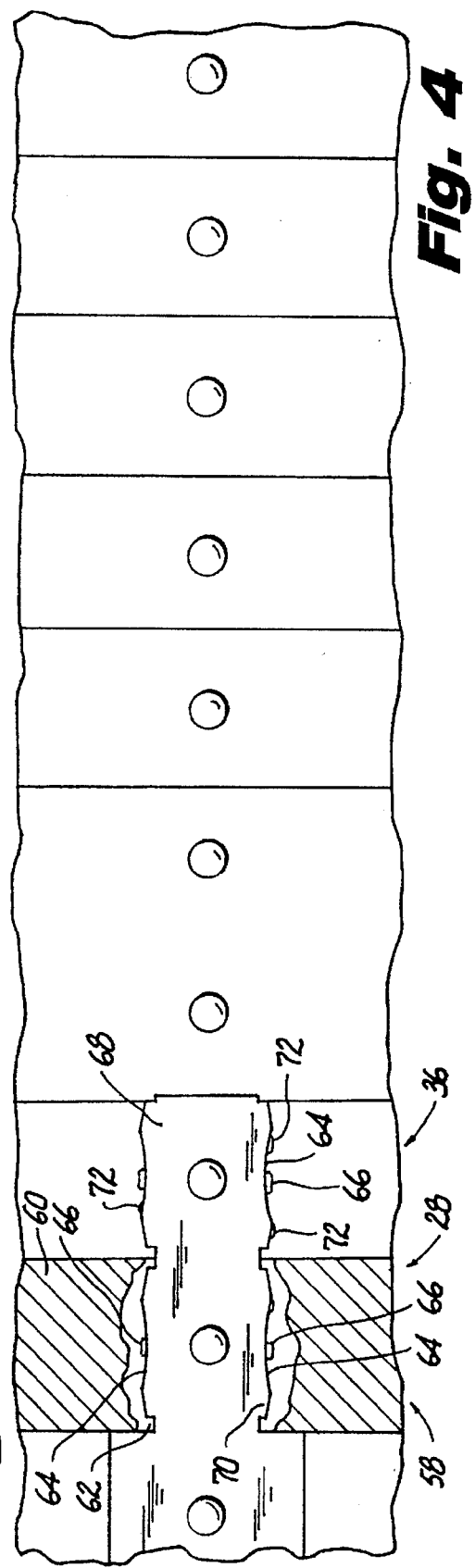

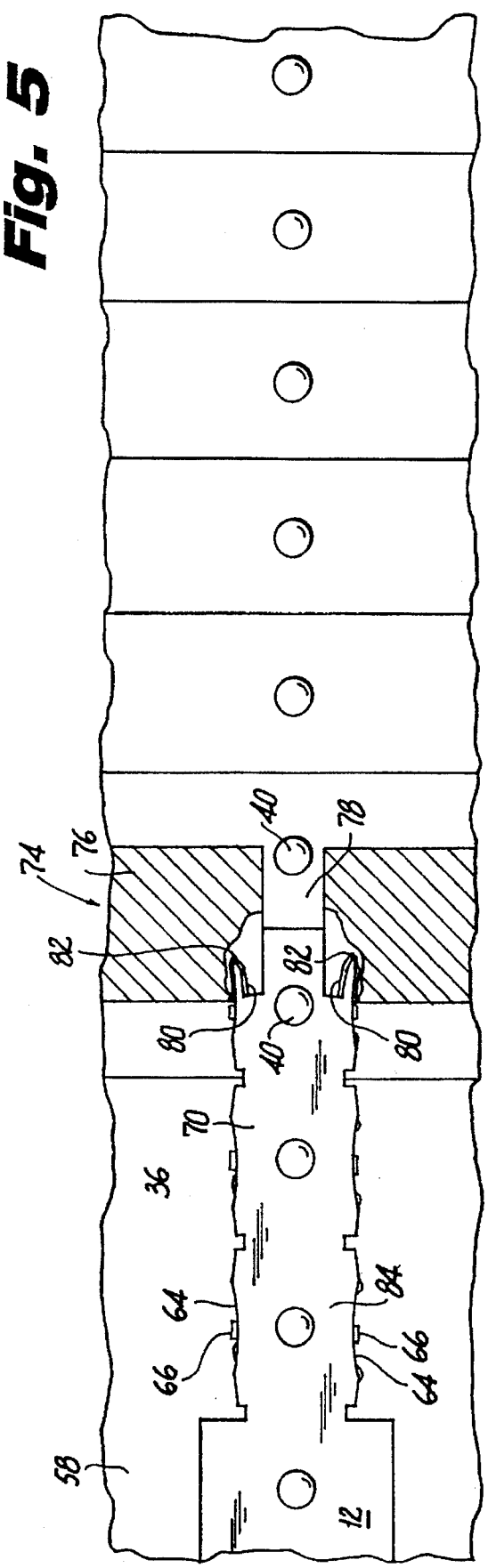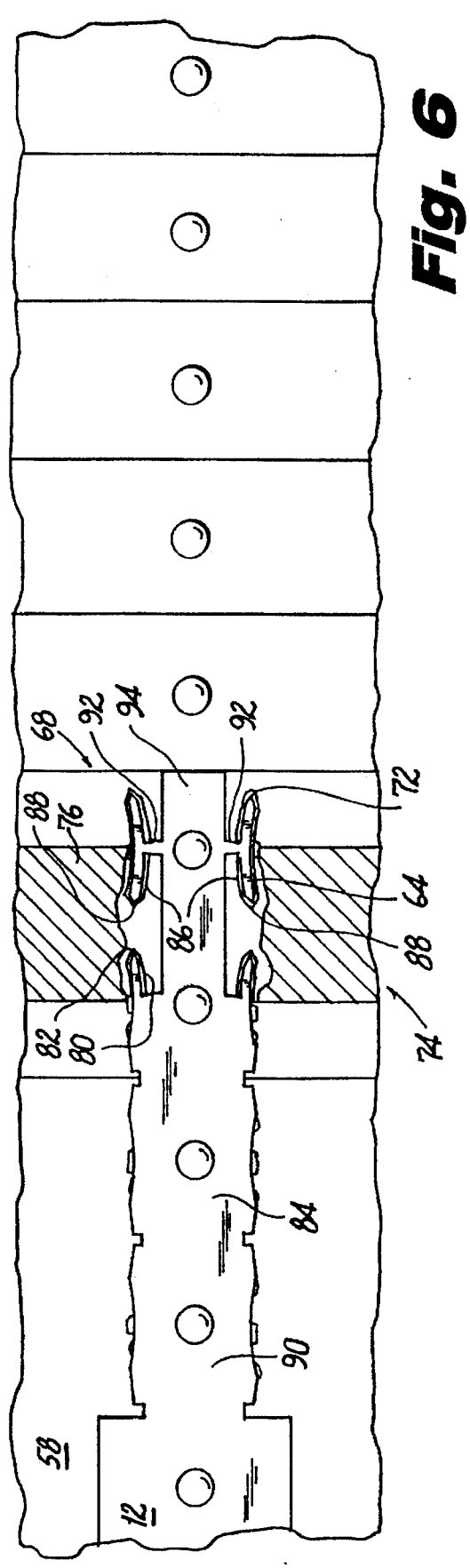

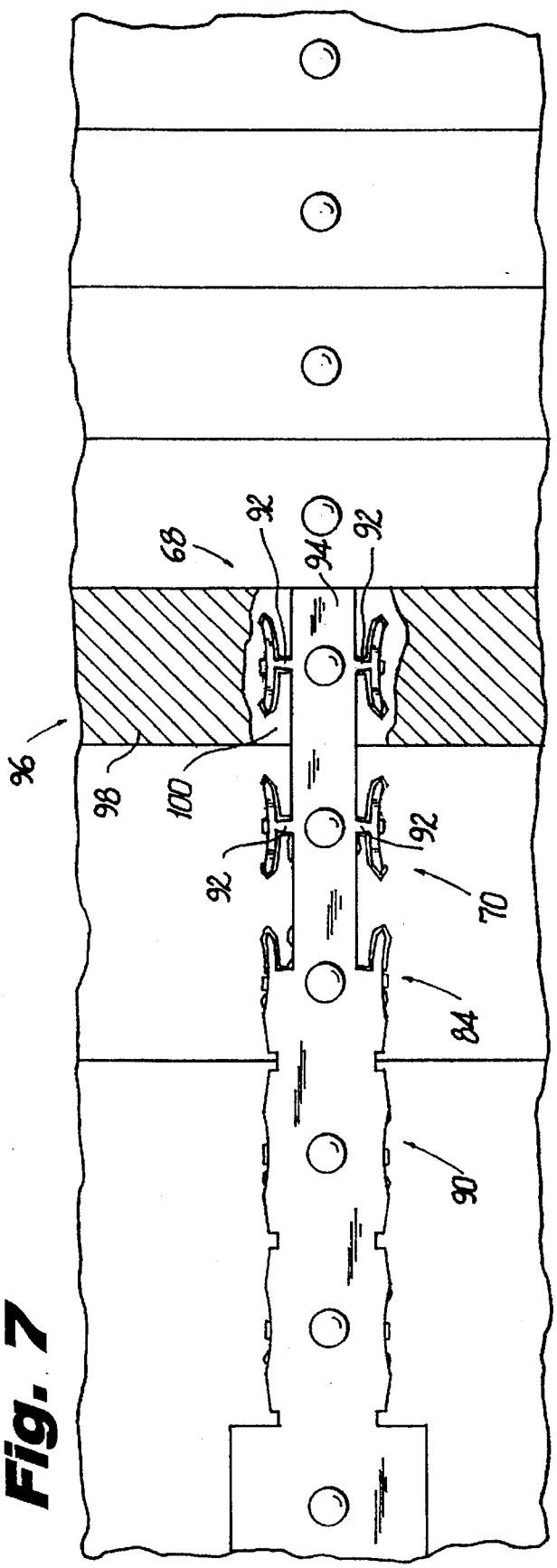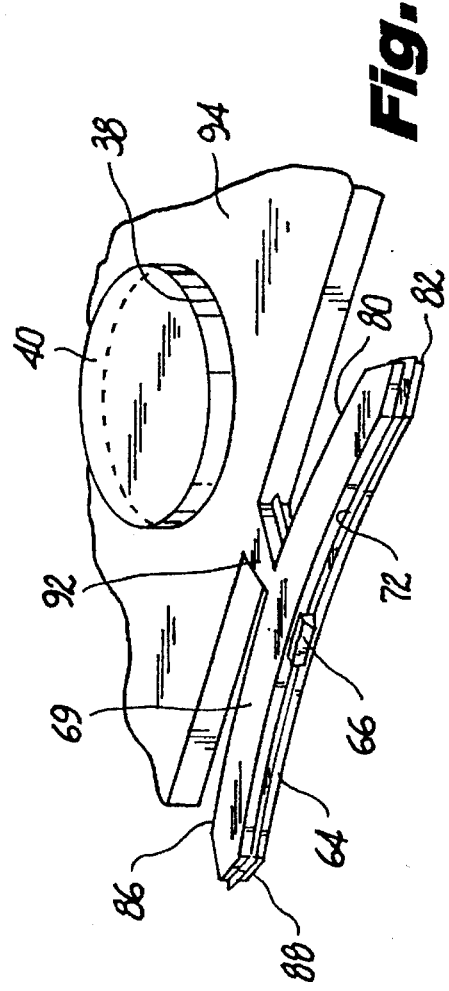

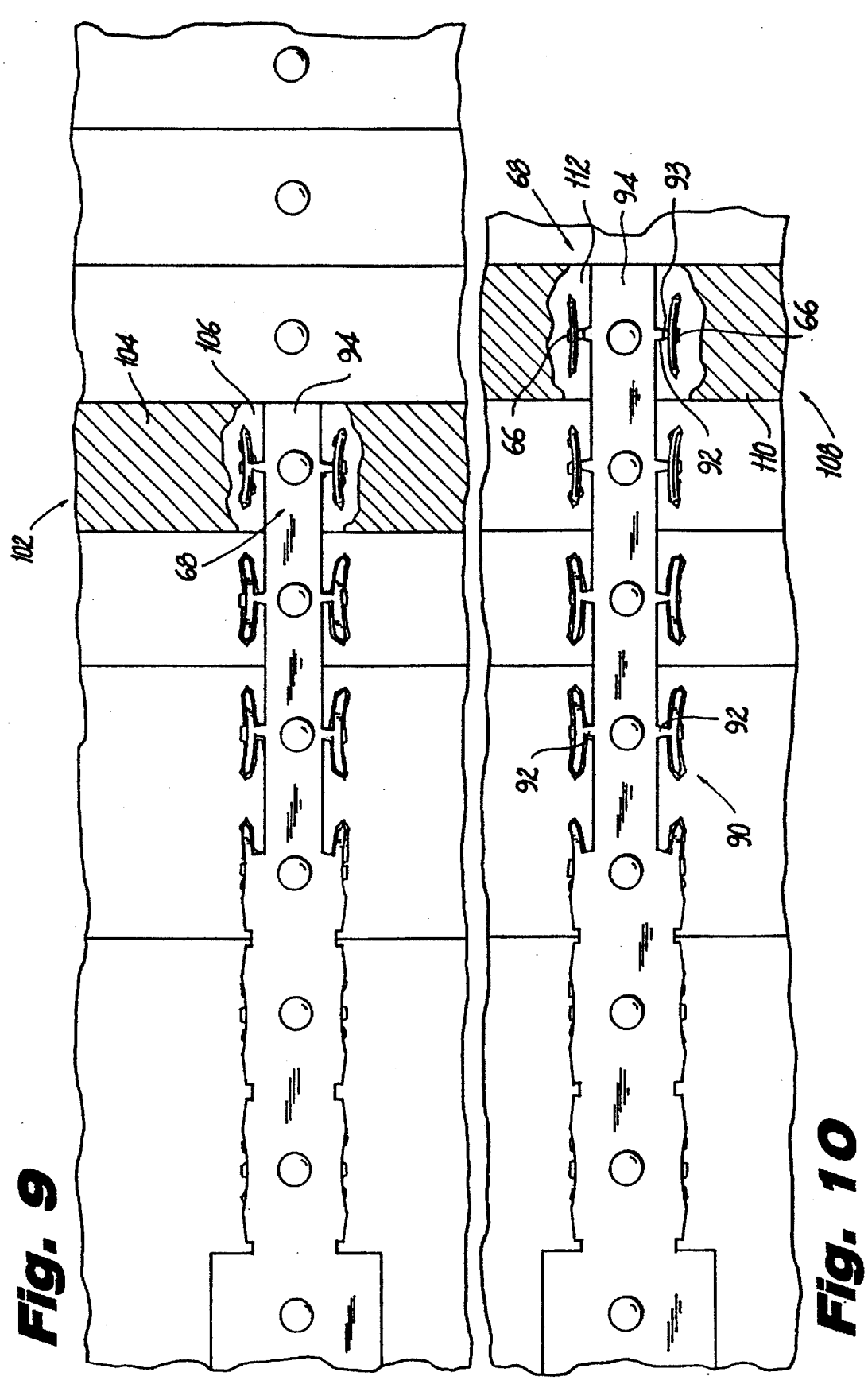

PROGRESSIVE DIE/CARRIER APPARATUS AND METHOD OF FORMING SURGICAL NEEDLES AND/OR INCISION MEMBERS

BACKGROUND

1. Technical Field

This disclosure relates generally to surgical needle forming and, more particularly, to a progressive die apparatus and method for forming high strength surgical needles, such as surgical incision members, from needle stock material, and the resulting surgical needles or surgical incision members.

2. Description of Related Art

Surgical incision members are surgical grade suturing needles having points formed at one or both ends and preferably include surgical suturing apparatus engagement structure formed within a body portion of the needle intermediate the pointed ends. Particular surgical incision members are disclosed in commonly assigned U.S. patent application Ser. Nos. 08/260,579, filed Jun. 16, 1994 now U.S. Pat. No. 5,569,301 entitled SURGICAL INCISION MEMBERS; 29/024,594, filed Jun. 16, 1994 now abandoned entitled SURGICAL INCISION MEMBER; 06/954,013 filed Sep. 30, 1992, now abandoned entitled SUTURING APPARATUS; and 08/134, 145 filed Oct. 8, 1993, now abandoned, entitled SURGICAL SUTURING APPARATUS WITH LOADING MECHANISM, the disclosures of which are incorporated by reference herein. The suturing apparatus engagement structure is provided in the body portion of the surgical incision members to cooperate with corresponding engagement structure, such as, for example, needle engaging members or blades, on various surgical suturing apparatus. One particularly suitable apparatus for manipulation of surgical incision members is disclosed in commonly assigned U.S. patent application Ser. No. 08/134,145 filed Oct. 8, 1993, now abandoned, entitled SURGICAL SUTURING APPARATUS WITH LOADING MECHANISM, the disclosure of which is incorporate by reference herein. Apparatus engagement structure in the body portion of the needle blank along with cooperating engagement structure on the surgical suturing apparatus facilitates repeatedly passing the surgical incision member between a pair of arms or jaws in the suturing apparatus. In this manner the surgical suturing apparatus is able to securely and precisely control the surgical incision member for very effective, rapid and precise suturing of tissue. The apparatus engagement structure may be in the form of notches, holes, or crimps, etc., formed in the body portion of the surgical incision member.

Additionally, surgical incision members may have various suture attachment structure formed in the body portion intermediate the pointed ends. Preferably, the suture attachment structure is positioned intermediate the apparatus engagement structure. The surgical incision members may be curved with a radius substantially equal to the distance between a pivot point and engagement structure on a pair of jaws. Alternatively, the surgical incision member may be relatively straight to facilitate transfer of the surgical incision member between a pair of parallel moving jaws or arms. The parallel moving arm or jaw structure may be in the form of arms or jaws which move perpendicular to each other axis or parallel to each other. One or both jaws of the suturing apparatus may move.

Due to the added manufacturing equipment necessary to produce apparatus engagement and suture attachment structure within the body portion of a needle, the manufacture of surgical incision members may often become complicated and costly. For example, one method of manufacturing the surgical incision member is by a process called metal injection molding or "MIM". The MIM manufacturing process tends to be costly and thus may adversely affect the otherwise desirable characteristics and traits of a surgical suturing apparatus utilizing surgical incision members.

The production of needles in general involves many processes and different types of machinery in order to prepare quality needles from raw stock. These varying processes and machinery become more critical in the preparation of surgical grade needles where the environment of intended use is in humans or animals. Some of the processes involved in the production of surgical grade needles include, inter alia, straightening wire stock, cutting needle blanks from the wire stock, tapering or grinding points on one or both ends of the blank, and providing structure for receiving a suture thread at an end of the blank or at a location intermediate the ends. As used herein, the term "needle blank" refers to a piece of needle stock material at various stages of completion but not fully formed into a surgical grade needle suitable for use during surgical procedures. Additionally, one skilled in the art will appreciate that flat surfaces may be formed on sides of the blank, typically by flat pressing portions of the needle blank to facilitate grasping by surgical instrumentation. Curving of the needle blank may also be performed where curved needles are desired. When providing curved needles for surgical procedures it is desirable for the needles to have a specified curvature, i.e., a predetermined radius of curvature. The desired radius of curvature for the finished needle varies with specific applications.

Surgical needles or surgical incision members formed by the MIM process or from wire needle stock material may lack certain characteristics found desirable when used in tough body tissues. These characteristic may include point sharpness, resistance to bending, ductility, etc. Bend strength may be compromised when it is desirable to maintain a specified ductility.

Surgical incision members, in particular, typically require several processes to form the finished product. These processes may include cutting and curving needle stock material to form needle blanks, altering or refining the tip configurations and curvature radius, punching or drilling the blank to form a suture hole and/or notching the blank to provide engaging structure for cooperative instrumentation. However, as noted above, when the surgical incision members are formed from wire needle stock material the resultant bend strength may be insufficient where the intended use of the needle is in tough tissues, such as, for example, ligaments and tendons, such as Cooper's ligament overlying pelvic bone Conventional needle processing is, in large part, a labor intensive operation requiring highly skilled labor and sophisticated machinery. One disadvantage to conventional needle processing is that most needle processing operations, such as, for example, cutting the blanks from stock, tapering the stock to form points, flat and side pressing of the body portion of the blanks, curving the blanks, notching, hole drilling, etc., are performed in batch operations on separate processing machines. One particular suitable progressive die apparatus for performing multiple operations on a single machine to produce surgical incision members is disclosed in commonly assigned U.S. patent application Ser. No. 08/320,015, filed Oct. 7, 1994, now Pat. No. 5,553,447, entitled PROGRESSIVE DIE APPARATUS FOR FORMING SURGICAL INCISION MEMBERS, the disclosure of which is incorporated by reference herein. This apparatus progressively forms a single needle at a time.

In some instances, during surgery a sharply pointed needle has been found to stick into or catch edges of bone resulting in over penetration and dulling of the needle point. Thus, it would be desirable to have an apparatus for progressively forming a large number of high strength surgical needles and, in particular, surgical incision members, resistant to dulling or bending through tough tissue or when bone is contacted. It also would be desirable to provide an apparatus and method for forming a large number of high strength surgical needles from needle stock material in a very short time and with a minimal amount of machinery. It would also be desirable to have an apparatus and method of imparting a predetermined optimal point geometry to a needle blank. It would further be desirable to have an apparatus and a method of progressively forming opposed pairs of curved surgical incision members having a desired radius of curvature. It would be still further desirable to have an apparatus and a method of simultaneously imparting apparatus engagement structure and drill point guide holes, or suture attachment structure, in the body portion of opposed pairs of surgical incision members. It would be especially desirable to provide a high strength surgical needle suitable for use in tough body tissues. It would be further desirable to provide a surgical needle having an optimal point/tip geometry.

SUMMARY

There is disclosed an apparatus and a method for progressively forming high strength surgical needles from bulk needle stock material. There are also disclosed high strength surgical needles formed on the apparatus or according to the disclosed method.

The apparatus generally includes first and second sets of dies which cooperate to form a series of progressive needle processing stations. A first series of needle processing stations removes material from needle stock material to rough form needle blanks attached to a carrier strip while a second series of processing stations refine the rough formed needle blanks attached to the strip into the desired configuration of surgical needles. The needle blanks are refined in the second processing stations without removing a further significant amount of material.

In particular, the first processing stations cut away or gut the needle stock material to roughly approximate the form of inner and outer edges of generally rectangular bodied needle blanks attached to a carrier snip. Initial points are also formed on the needle blanks. Preferably, the inner and outer edges are curved and define a predetermined radius of curvature to the needle blank where curved finished needles are desired. Further, it is preferable to simultaneously rough form, and subsequently process, mirror image opposed pairs of needle blanks formed on an adjacent side of the carrier strip.

The second processing stations refine the rough formed needle blanks by compressing or coining the rough formed rectangular bodied needle blanks into needle blanks having a predetermined cross-section and one or more points. Preferably, the cross-section is substantially circular while the point is substantially conical and has an optimized tip radius for penetrating tissue but which will not become imbedded in bone. Where surgical incision members are desired, conical points are formed at both ends of the needle blank. Typically, the second processing stations each include a first die station for imparting the desired configuration and a second station to refine or qualify the previously imparted configuration.

Additionally, stations are provided to impart apparatus engagement structure in the form of notches adjacent either end and suture attachment structure in the form of a hole, intermediate the notches, into a body portion of the needle blanks.

Finally, severing stations are provided to either sever individual needles from the carrier strip or to sever a portion of the carrier strip containing attached surgical needles. Surgical needles formed on the above apparatus have been found to have a significantly higher bend strength than those formed from wire stock or by MIM processes while retaining desired ductility.

The disclosed method generally includes the steps of gutting needle stock material to rough form needle blanks attached to a carrier strip and progressively coining the rough formed blanks into surgical needles. The gutting step includes removing material from the needle stock material to form outer and inner edges of a rough needle blank with rough points at either end. A portion or leg of material is left connected to the rough formed blank while the remainder of the needle stock material forms a carrier strip of material.

The coining step generally includes compressing the rough formed needle blank between progressive pairs of dies to impart a generally circular cross-section to the body portion and a conical point on at least one end.

The method may further include the steps of notching an edge of the needle blank to form apparatus engagement structure and forming a hole in the needle blank to form suture attachment structure.

Finally, there is disclosed a high bend strength surgical needle formed on the disclosed apparatus or by the disclosed method. Preferably, the surgical needle is a surgical incision member having a predetermined radius of curvature and an optimized conical radius at the tips. The surgical incision member may also include suture attachment structure as well as apparatus engagement structure.

BRIEF DESCRIPTION OF THE DRAWINGS

Various embodiments are described herein with reference to the drawings, wherein:

FIG. 3 is a top plan view of the needle forming stations of the apparatus of FIG. 1 illustrating a first die station forming an initial inner radius of curvature to an opposed pair of needle blanks;

FIG. 4 is a top plan view similar to FIG. 3 illustrating the formation of inner radius of curvature to oppose pairs of needle blanks similar to FIG. 3 and an adjacent skip station;

FIG. 5 is a top plan view similar to FIG. 3 illustrating a second die station for forming points and an outer radius of curvature on a first opposed pair of needle blanks;

FIG. 6 is a top plan view similar to FIG. 5 illustrating points and outer radius of curvature being formed in both first and second opposed pairs of needle blanks;

FIG. 7 is a top plan view illustrating a third die station for qualifying the roughed formed needle blanks into opposed pairs of rectangular bodied needle blanks attached to the carrier strip;

FIG. 8 is an enlarged perspective view of one of the needle blanks of FIG. 7;

FIG. 9 is a top plan view illustrating a fourth die station imparting a substantially round cross-sectional profile to the opposed pairs of needle blanks of FIG. 7;

FIG. 10 is a view similar to FIG. 9 of a fifth die station qualifying the circular cross-section formed by the fourth die station;

DETAILED DESCRIPTION OF PREFERRED EMBODIMENTS

The present progressive die apparatus is designed to progressively form surgical needles and, in particular, surgical incision members from needle stock material. The apparatus has a series of processing stations or die sets which generally perform two distinct types of operations. In the first, material is removed or gutted from the needle stock material to rough form an opposed pair of needle blanks attached to the needle stock material, the remainder of which forms a carrier strip. In the second, the rough formed blanks are compressed or coined to form the finished surgical needles. The carrier strip functions to progressively advance the opposed pair of blanks through the apparatus.

Figure 1:
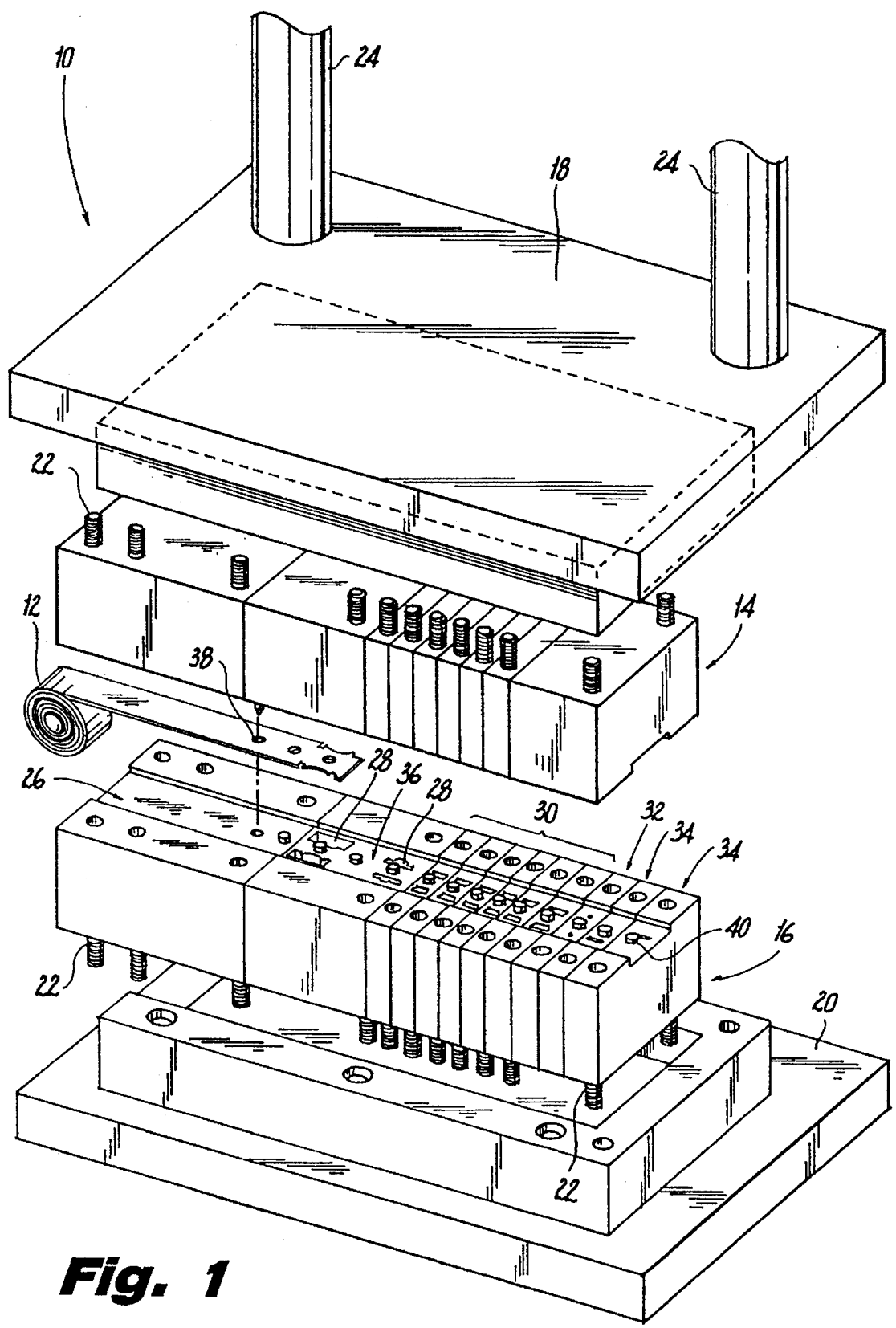
FIG. 1 is a perspective view of a progressive die apparatus for forming surgical incision members with upper and lower portions separated.

Referring now to FIG. 1, a preferred embodiment of the progressive die needle forming apparatus 10 is illustrated. As noted above, apparatus 10 is particularly suited to form opposed pairs of needle blanks from bulk needle stock material such as flat needle stock material 12. Preferably, needle stock material 12 is 301 stainless steel. Apparatus 10 is provided with a plurality of needle processing die stations, each of which contains corresponding upper and lower dies. The upper and lower dies are arranged in removable block arrangements and generally consist of an upper die block set 14 and a lower die block set 16. The individual dies within upper and lower block sets 14 and 16, respectively, are interchangeable to provide flexibility in the needle forming processes.

Upper die block set 14 is affixed to a movable top plate 18 while lower block set 16 is fixedly held within a base plate 20. Upper die block set 14 and lower die block set 16 are removably fastened to top plate 18 and base plate 20, respectively, by means of fasteners 22. Fasteners 22 may be of the threaded screw variety illustrated or any other suitable fasteners which allows secure yet removable retention of the respective dies within the respective die block sets. In order to process needle stock material 12, a pair of press bars 24 are affixed to top plate 18 and function to move top plate 18 in a vertical direction to bring upper die block set 14 toward lower die block set 16 and compress needle stock material 12 positioned therebetween.

In general, the needle processing stations include a pilot hole forming station 26, gutting stations 28 which are used to rough form an opposed pair of needle blanks, and one or more coining stations 30 which are used to shape and refine the rough formed needle blank into a finished needle. Additionally, a forming station 32 may be provided to impart apparatus engagement structure and a suture attachment hole or other suture retaining structure into the fully formed needle blanks, as described in more detail hereinbelow. One or more severing stations 34 may also be provided to separate the needle blanks from the remaining bulk needle stock material or carrier strip. Additionally, as illustrated, one or more skip stations 36 may be provided which perform no processing functions on a needle blank. Skip stations 36 fill up space taken in the absence of an actual processing station and provide room on apparatus 10 for additional processing stations or die sets, as desired for future modifications or refinements. As noted above, pilot hole forming station 26 is provided which imparts a series of guide holes 38 in needle stock material 12. Guide holes 38 cooperate with guide pins 40 formed in lower die block set 16 to ensure precise indexing of needle stock material 12 as the needle stock material 12 is advanced through apparatus 10.

Apparatus 10 simultaneously and progressively forms opposed pairs of needle blanks from needle stock material 12. Thus, while one or a leading opposed pair of needle blanks is being processed at one station, a next adjacent following opposed pair of needle blanks is simultaneously processed at the station behind the leading pair.

Figure 2:
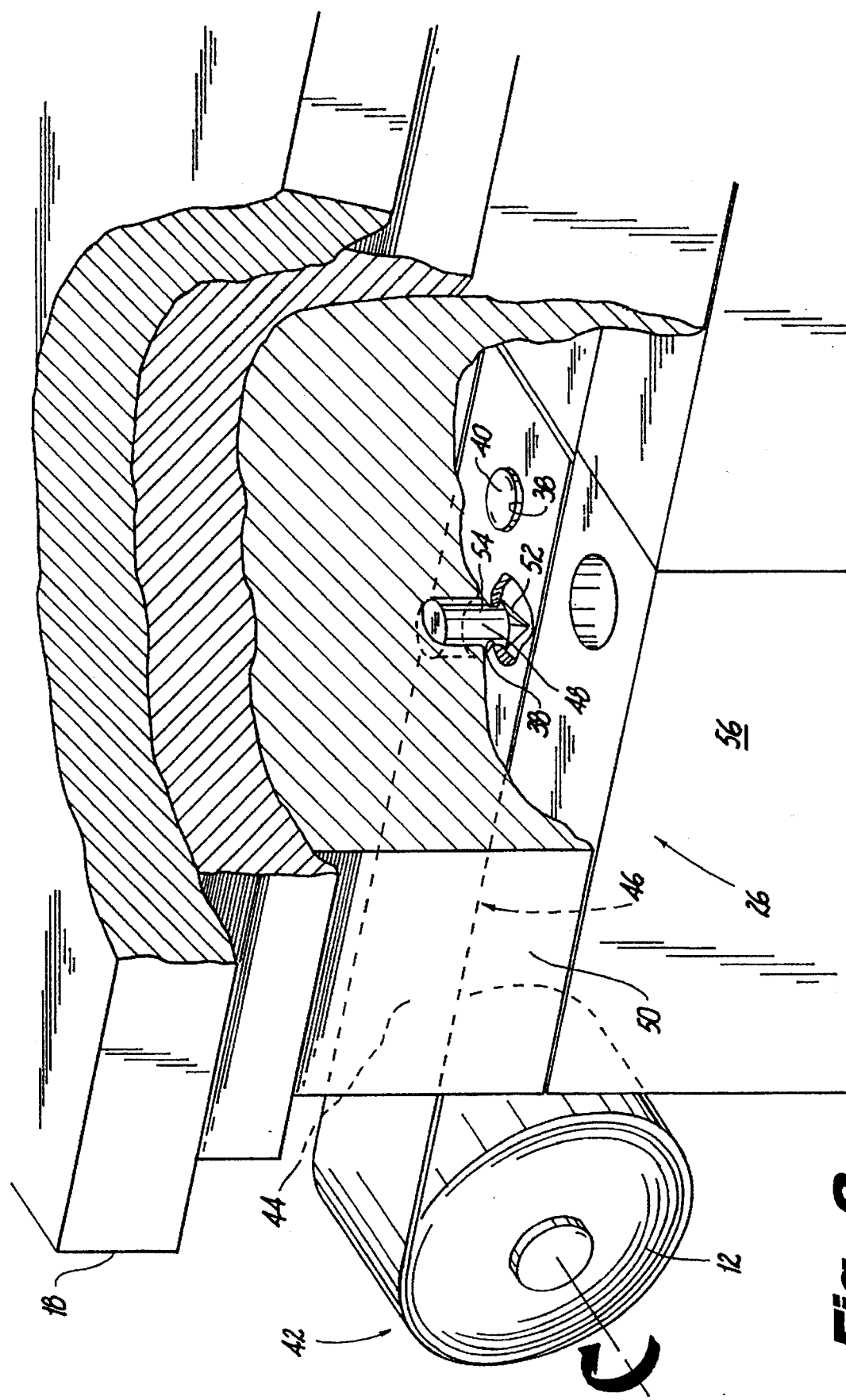
FIG. 2 is an enlarged perspective view, partly shown in section, of the apparatus of FIG. 1 illustrating a preliminary die station for imparting pilot holes to a flat strip of needle stock material.

Referring now to FIG. 2, pilot hole forming station 26 is provided to impart a series of guide holes 38 within needle stock material 12. As noted above, guide holes 38 cooperate with guide pins 40 to insure proper indexing of needle stock material 12 with respect to the processing stations as the needle stock material is advanced through apparatus 10. When the needle stock material 12 is provided in a roll form it is preferable to straighten needle stock material 12 prior to processing into needle blanks. Thus, needle stock material 12 will generally include a roll portion 42 which is progressively straightened into straightened portions 44 in a straightening area 46 of pilot hole forming station 26. While the preferred form of needle stock material 12 is in a roll of flat strip form, it will be appreciated by those skilled in the an than any suitable bulk needle stock material may be used in the gutting and coining processes disclosed herein, including sheet stock.

Once straightened portion 44 has been formed it is advanced beneath a punch pin 48 formed in upper die 50. Upper die 50 along with a lower die 56, described hereinbelow, form the upper and lower dies for pilot hole forming station 26. Punch pin 48 is preferably provided with a pointed tip 52 which is driven through flattened portion 44 into a recess 54 on a lower die 56 to thereby punch a guide hole 38 in straightened portion 44 of needle stock material 12. Guide holes 38 are evenly spaced to cooperate with evenly spaced guide pins 40 thereby ensuring accurate indexing of opposed pairs of needle blanks as they are advanced through apparatus 10.

After punching guide hole 38, upper plate 18 is raised and needle stock material 12 is advanced further into apparatus 10. Needle stock material 12 is biased upwardly against upper die block set 14. Thus, upon raising top plate 18, flattened portion 44 of needle stock material 12 and thus guide holes 38 are lifted off of guide pins 40. On subsequent advancement and lowering of needle stock material 12 and top plate 18, a following guide hole 38 will be moved down onto the guide pin 40 previously holding a lead guide hole 38. Thus, needle stock material 12 may be incrementally advanced through apparatus 10 and indexed with respect to the processing stations. After guide holes 38 have been formed within flattened portion 44 of needle stock material 12 that portion of needle stock material 12 may be incrementally advanced into apparatus 10 to begin the actual progressive needle forming processes.

Referring now to FIG. 3, after pilot hole 38 has been formed in flattened portion 44, top plate 18 is raised and the needle stock material advances further into apparatus 10. Flattened portion 44 is advanced such that, upon downward vertical movement of top plate 18, guide holes 38 are aligned above guide pins 40 thus insuring proper indexing of needle stock material 12 between the die sets. As noted above, gutting die stations 28 are provided to initially remove material from needle stock material 12. A first gutting die station 58 includes an upper die 60 and a lower die 62. A portion of upper die 60 engaging needle stock material 12 has been cut away to illustrate the forming operation performed on needle stock material 12. Upper and lower dies 60 and 62, respectively, are gutting dies of the type known in metal swaging and forming arts. Upper die 60 includes a male die face (not shown) while lower die 62 includes a female die face (also not shown) and between which material of needle stock material 12 is gutted or removed. While the actual die faces are not shown it is well within the skill of those skilled in the art to construct the die faces so as to impart the described and illustrated shapes and profiles to needle stock material 12.

Once a guide hole 38 has been positioned on guide pin 40 that portion of flattened needle stock material 44 is compressed between upper and lower dies 60, 62 respectively. Material is removed from needle stock material 12 resulting in inner radial edges 64 formed on opposing sides of needle stock material 12. Inner radial edges 64 are the rough formed inner radial edges of a leading pair of opposed needle blanks to be formed from needle stock material 12. Preferably, upper and lower die sets 60, 62 also leave a sufficient amount of material along inner radial edge 64 to pre-form crimp bulges 66 centrally located on inner radial edges 64.

Thus, a first gutting operation has been performed on needle stock material 12. To continue the progressive formation of needle blanks, top plate 18 is again raised and needle stock material 12 advanced further into apparatus 10.

Referring now to FIG. 4, needle stock material 12 is advanced one unit further into apparatus 10. As used herein, the term "advanced" includes raising upper plate 18, lifting needle stock material 12 and thus guide holes 38, off of guide pins 40 and advancing needle stock material 12 the distance between one set of guide pins 40. Thus, a subsequent processing operation requires the lowering of top plate 18 to position the guide hole 38 associated with a particular pair of opposed needle blanks on the next adjacent guide pin 40 to index that portion of needle stock material 12 between the next die stations.

As shown in FIG. 4, upon pressing top plate 18 against bottom plate 20 a second, or first following, pair of opposed inner radial edges 64 and crimp bulges 66 are formed in needle stock material 12 within gutting station 28. At this point, the leading opposed pair of needle blanks 68 are positioned within a skip station 36, which, as noted hereinabove, provides no additional processing function on needle stock material 12. The inner radial edges 64 and crimp bulges 66 formed in this second operation of first gutting die station 58 are the initial formation of a first following opposed pair of needle blanks 70 which will sequentially follow the leading opposed pair 68 throughout subsequent processing on apparatus 10. As noted above, during the gutting operation, a portion of needle stock material 12 is being removed and needle blanks are being rough formed. Thus, as one would expect, a certain amount of flash 72 may result along edges of the needle blanks. Flash 72 will be removed in later forming steps as described more fully in detail hereinbelow.

Referring now to FIG. 5, on the next vertical cycling of apparatus 10 needle stock material 12 is advanced to position the leading opposed pair 68 partially beneath a second gutting die station 74. It will be noted that second gutting die station 74 is positioned to impact its dies intermediate a pair of guide pins 40. Thus, upon cycling apparatus 10, second gutting die station 74 engages only a portion of an opposed pair of needle blanks. Second gutting die station 74 consists of an upper die 76 and a lower die 78 which are configured and dimensioned to remove material from needle stock material 12 resulting in a first outer radial edge 80 of an opposed pair of needle blanks. Additionally, upper and lower dies 76 and 78 form first points 82 in the opposed pair of needle blanks. As shown, the first following opposed pair 70 is positioned within the skip station 36 while a second following opposed pair 84 is being simultaneously formed with inner radial edges 64 and crimp bulges 66 within the first gutting die station 58. Thus, on each cycling of apparatus 10 a new part of needle stock material 12 is being progressively formed into needle blanks simultaneously with the processing of the preceding needle blanks.

Referring now to FIG. 6, on the next cycling of apparatus 10 needle stock material 12 is advanced and second gutting die station 74 impacts intermediate the leading opposed pair 68 and the first following opposed pair 70. At this point, upper and lower dies 76, 78 are operating on portions of four needle blanks simultaneously. As shown, a second outer radial edge 86 along with a second point 88 is formed in the leading opposed pair 68. At the same time, first outer radial edges 80 and points 82 are being formed in the first following opposed pair of blanks 70. Thus, leading opposed pair 68 have been rough formed into needle blanks connected to the remaining material of needle stock material 12 by a leg 92 defined between the first and second outer radial edges 80, 86, respectively. The resulting portion of needle stock material 12, intermediate the opposed pair of needle blanks and containing guide holes 38, forms a carrier strip 94 which will be utilized to support and transport the opposed pairs of needle blanks through apparatus 10. As shown, simultaneously, a third following opposed pair of needle blanks 90 is initially rough formed within first gutting die station 58.

In the previous gutting operations material was removed from needle stock material 12 to rough form an opposed pair of needle blanks such as, for example, blanks 68 connected to carrier strip 94 by legs 92. In the subsequent needle forming operations the needle blanks will be compressed or coined to reshape the material attached to carrier strip 94 rather than to remove any excess material with the possible exception of the removal of flash 72.

Referring now to FIG. 7, a first coining die station 96 includes an upper die 98 and a lower die 100. First coining die station 96 is provided to refine or qualify the rough formed shape of the leading opposed pair of needle blanks positioned therein. Since up to this point the needle blanks have been formed from the sheet of flat needle stock material 12 the needle blanks, for example, leading opposed pair of needle blanks 68, have a generally rectangular cross-section. As described in more detail hereinbelow, by initially gutting needle stock material 12 into needle blanks having a rectangular cross-section and a predetermined radius of curvature, the resultant surgical needles have a significantly higher bend strength than those needles formed from initially straight circular cross-section wire stock and bent or those needles formed by the MIM process. First coining die station 96 does not alter this rectangular cross-section as most clearly illustrated in FIG. 8.

As shown in FIG. 8, one needle blank 69 of the leading opposed pair 68 includes an inner radial edge 64 having a crimped bump 66 formed thereon and outer radial edges 80 and 86. Points 82 and 88 are formed on opposite ends of blank 69 and blank 69 is connected to carrier strip 94 by means of leg 92. At this stage a significant amount of flash 72 remains on needle blank 69. The simultaneous operations of the gutting stations 58 and 74 and first coining die station 96 serve to rough form opposed pairs of needle blanks such as, for example, leading opposed pair of needle blanks 68 attached to carrier strip 94 by means of legs 92.

After a portion of needle stock material 12 has been rough formed into an opposed pair of needle blanks 68 having a rectangular cross-section, initial points 82, 88 and a predetermined radius of curvature, apparatus 10 may continue to be cycled to bring successive needle blanks 68 into engagement with subsequent processing stations. The subsequent stations will impart a circular cross-section to the needle blanks as well as refine the points into conical points. Additionally, subsequent processing stations may impart suture attachment structure, apparatus engagement structure, etc. into the needle blanks as well as remove any remaining flash. Of course, if desired, the body of the needle may be of rectangular cross section.

Referring now to FIG. 9, there is shown a second coining die station 102 which is configured to reshape and form the opposed pairs of needle blanks 68 into needle blanks having a substantially circular cross section without the removal of any additional needle blank material. Second die station 102 includes an upper die 104 and a lower die 106. Additionally, second coining die station 102 imparts an initial conical shape to opposed first and second points 82 and 88, respectively.

Referring to FIG. 10, a third coining die station 108 having upper die 110 and lower die 112 further refines or qualifies the substantially circular cross-section and conical shaped points formed in second coining die station 102. It will be noted that at this stage, third following opposed pair of needle blanks 90 have been rough formed into an opposed pair of needle blanks attached to carrier strip 94 by means of legs 92. Additionally, during processing at third coining die station 108, a portion of each leg 92 is impacted by upper and lower dies 110 and 112 respectively to begin reducing the cross-sectional area of legs 92. The reduced cross-sectional area 93 facilitates severing finished needles from carrier strip 94 and providing an additional crimping bulge. The reduced cross-sectional area 93 is located adjacent each needle blank and diametrically opposite crimping bulges 66.

As noted hereinabove, while the die faces of each of the upper and lower dies of each die station are not illustrated, it would be obvious to one skilled in the art how to construct and configure the particular die faces to either remove the needle stock material or impart particular configurations and profiles to the needle stock material in accordance with the present written descriptions and illustrations of each die or processing station.

Figure 11:
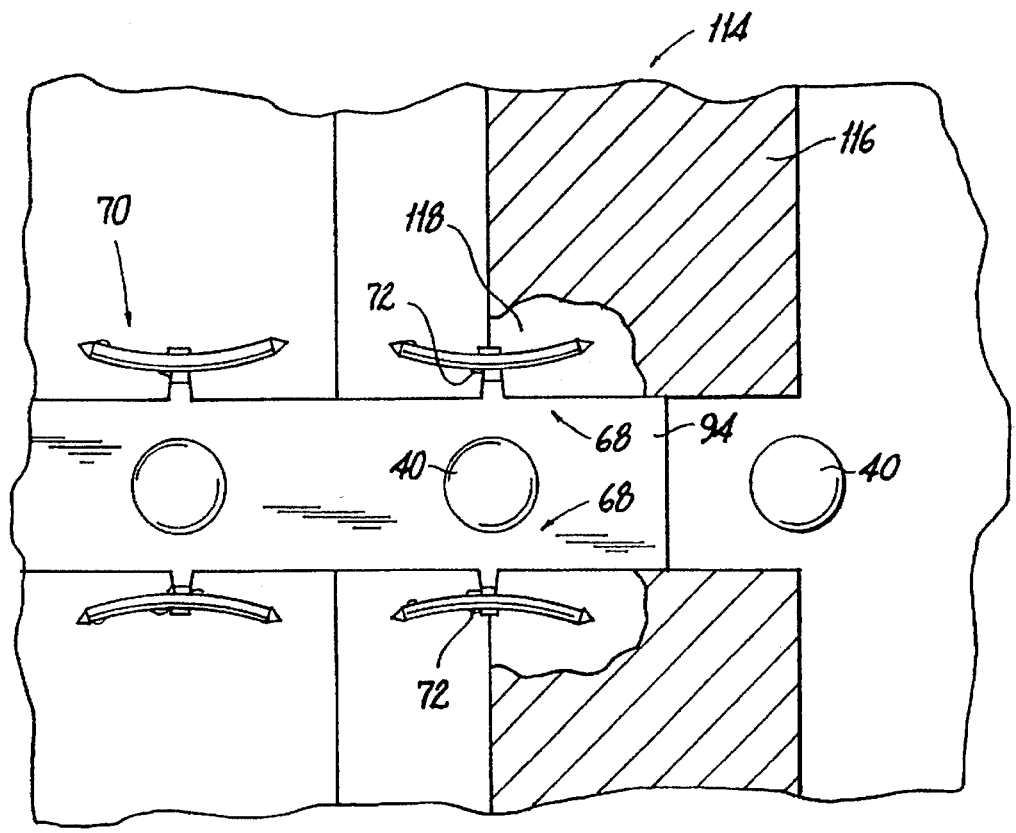
FIG. 11 is a top plan view illustrating a sixth die station removing flash from the first opposed pair of needle blanks.

Referring now to FIG. 11, there is illustrated a third gutting die station 114. Third gutting die station 114 is provided to qualify or further refine the cylindrical cross-section and conical tip radius of the opposed pair of needle blanks impacted thereby. Additionally, third gutting die station 114 is configured to remove excess flash 72 from the opposed pair of needle blanks. Third gutting die station 114 includes an upper die 116 and a lower die 118 which functions in a manner similar to dies 76 and 78 of second gutting die station 74. Specifically, as an opposed pair of needle blanks are advanced into third gutting die station 114, third gutting die station 114 impacts intermediate a pair of guide pins 40 thereby acting on only a leading or trailing portion of an opposed pair of needle blanks, for example, leading portions of leading pair of needle blanks 68, at a time.

Figure 12:
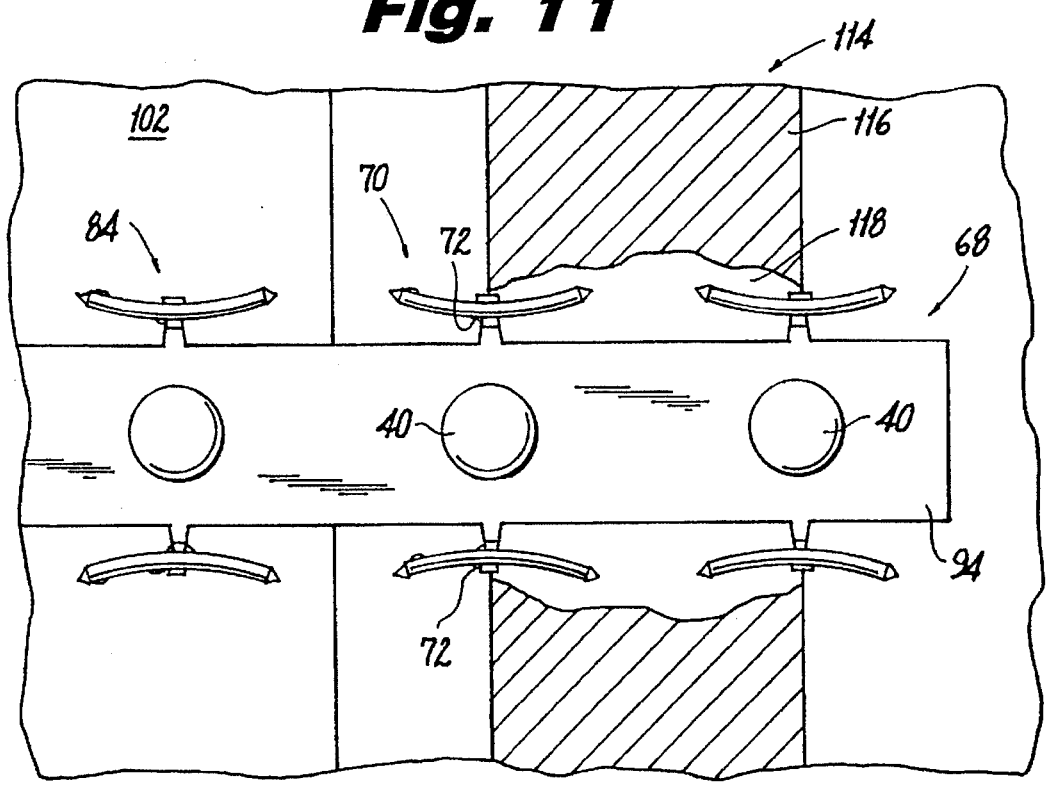
FIG. 12 is a view similar to FIG. 11 illustrating the sixth die station removing flash from portions of both the first and second opposed pairs of needle blanks.

Referring now to FIG. 12, as apparatus 10 is again cycled and carrier strip 94 is advanced, upper and lower dies 116 and 118 impact intermediate leading opposed pair of needle blanks 68 and first following opposed pair of needle blanks 70 to thereby qualify and further remove flash from those portions of the opposed pairs of needle blanks engaged thereby. As shown in FIGS. 11 and 12, second following opposed pair of needle blanks 84 have been imparted with a cylindrical cross-section and conical tapered points in second coining die station 102.

Figure 13:
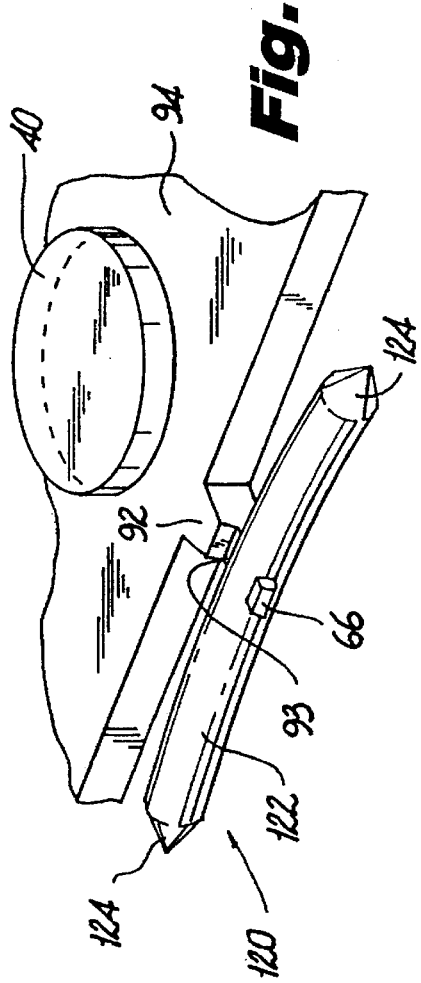
FIG. 13 is an enlarged perspective view of one of the needle blanks formed at the sixth die station.

Referring now to FIG. 13, there is depicted a finished surgical needle blank 120 attached to carrier strip 94 by means of leg 92. Needle blank 120 generally includes a cylindrical body portion 122 having conical radiused tips 124 at either end thereof. Preferably, needle blank 120 has an axial radius of curvature on the order of about 800 inches while the conical tips have a conical tip radius on the order of about 0.005 inches to 0.015 inches and preferably have a conical tip radius on the order of about 0.007 inches. As noted hereinabove, reduced cross-sectional portion 93 of leg 92 has been coined down to the approximate size of crimping bulge 66.

Needle blank 120 may be severed at this point by cutting through reduced portion 93 thereby resulting in individual surgical needle blanks suitable for hole drilling and tumbling. It will be appreciated that, while apparatus 10 has been illustrated and described as producing curved double-pointed needles from flat stock, it is within the contemplated scope of the disclosure, as well as within the skill of those in the art, to configure the die stations to form curved, straight, single or double pointed needles, as well as any combination thereof.

Figure 14:
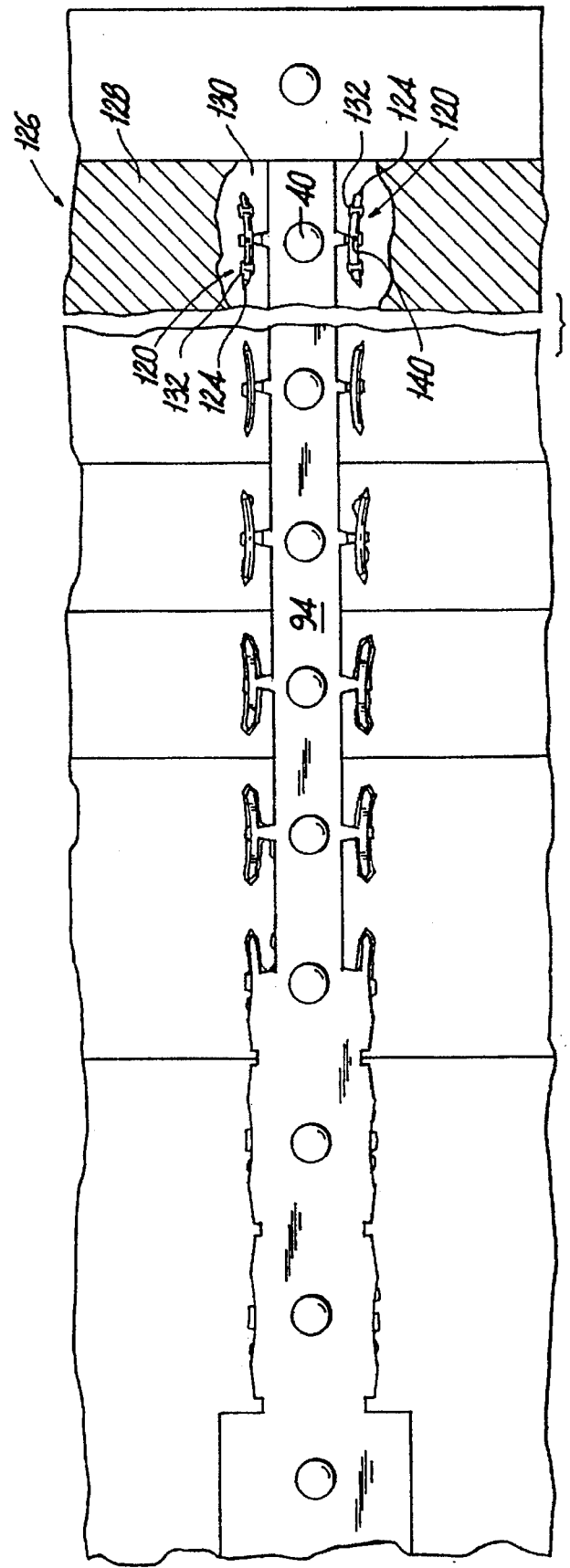
FIG. 14 is a top plan view illustrating a seventh die station for imparting apparatus engagement structure into opposed pairs of needle blanks and imparting pilot holes intermediate the apparatus engagement structure.

As shown in FIG. 14, where surgical incision numbers are desired to be formed on apparatus 10 it is preferable to provide a notching die station 126 having upper and lower dies 128, 130, respectively. Upper die 128 is configured to impart a pair of apparatus engagement notches 132 adjacent either conical end 124 of needle 120. A particular die for imparting the notches and accommodating the needle radius of curvature during notching is disclosed in U.S. Pat. No. 5,853,477, entitled PROGRESSIVE DIE APPARATUS FOR FORMING SURGICAL INCISION MEMBERS. Preferably, lower die 130 supports needle 120 and performs notch forming functions by itself.

Figure 15:
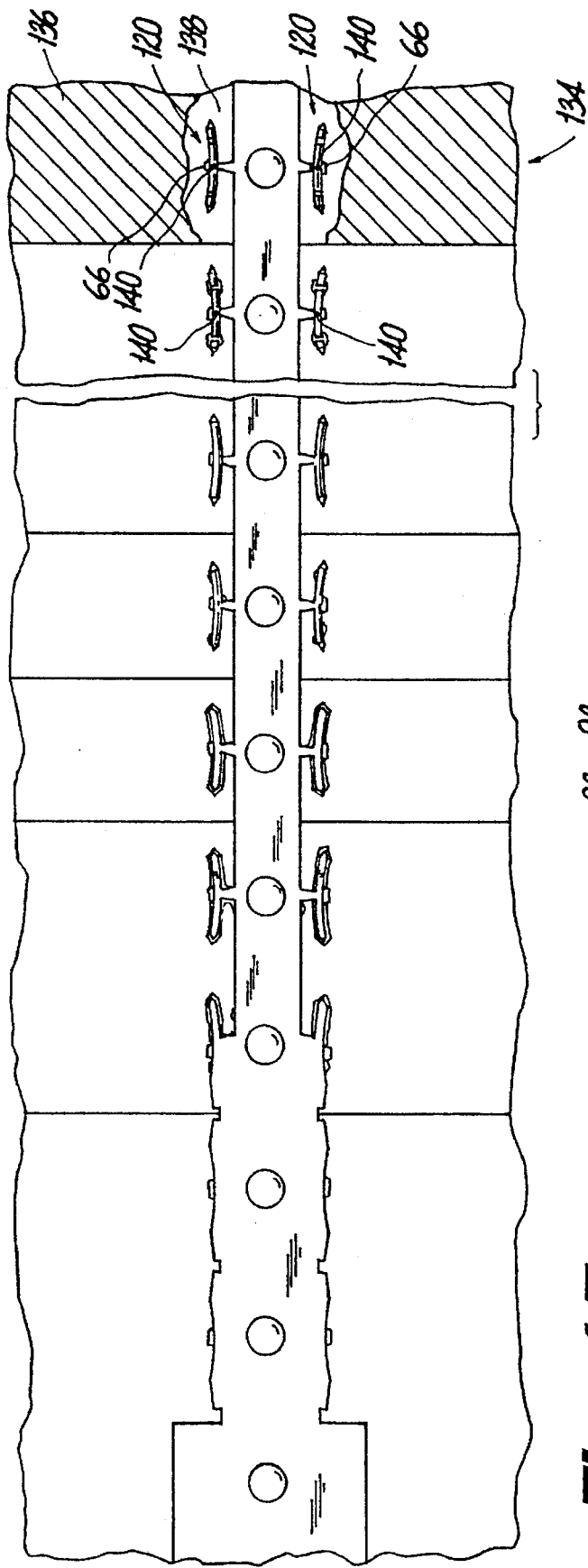
FIG. 15 is a top plan view illustrating an eighth die station qualifying the apparatus engagement structure and removing flash formed in the seventh die station.

Referring now to FIG. 15, there is shown an additional notching die station 134 having an upper die 136 and a lower die 138. Upper die 136 in conjunction with lower die 138 serve to further refine notches 126 and remove any flash 72 resulting from the impartation of the apparatus engagement structure notches into needles 120.

Referring for the moment to both of FIGS. 14 and 15, in a preferred embodiment of apparatus 10, notching die stations 126 and 134 are configured to impart dimples 140 to each of the opposed needles 120 to serve as pilot holes for future suture hole drilling. Preferably, dimples 140 are formed diametrically opposite on either side of needle 120 intermediate the apparatus engagement structure notches 132 and substantially adjacent crimp bulge 66 and reduced area portion 93. Dimples 140 are substantially perpendicularly oriented relative to bulges 66. By forming dimples on either side of needles 120, burring of the needle is reduced as the hole forming device penetrates through the needle.

Figure 16:
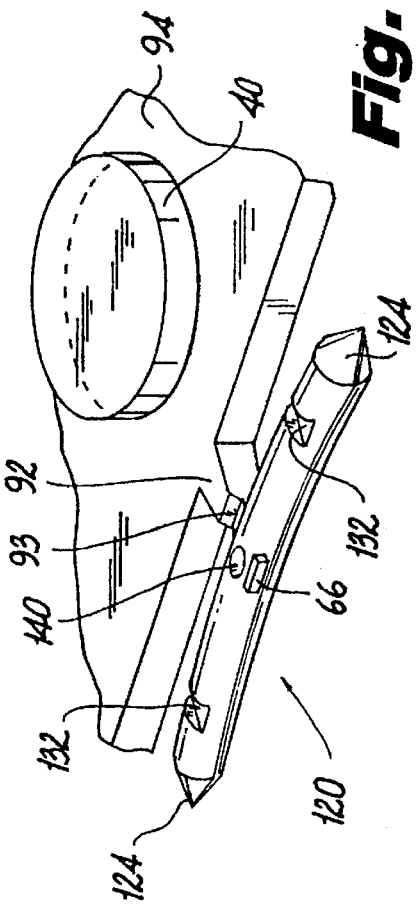
FIG. 16 is an enlarged perspective view of one of the needle blanks formed in the eighth die station.

Referring now to FIG. 16, there is illustrated a surgical incision member blank 120 having apparatus engagement structure or notches 132 formed adjacent either conical pointed end 124 thereof. Additionally, the surgical incision member has a crimping bulge 66 and dimples 140. Once blank 120 is provided with a suture attachment hole and severed from carrier strip 94 a surgical incision member is formed.

While the preferred embodiment of the apparatus 10 imparts dimples 140 into a pair of needle blanks simultaneously with apparatus engagement structure notches 132 being imparted into the same opposed pair of needle blanks, it is within the contemplated scope of the present disclosure to perform the acts of imparting apparatus engagement structure and dimples within an opposed pair of needle blanks in separate operations and at different processing stations.

Figure 17:
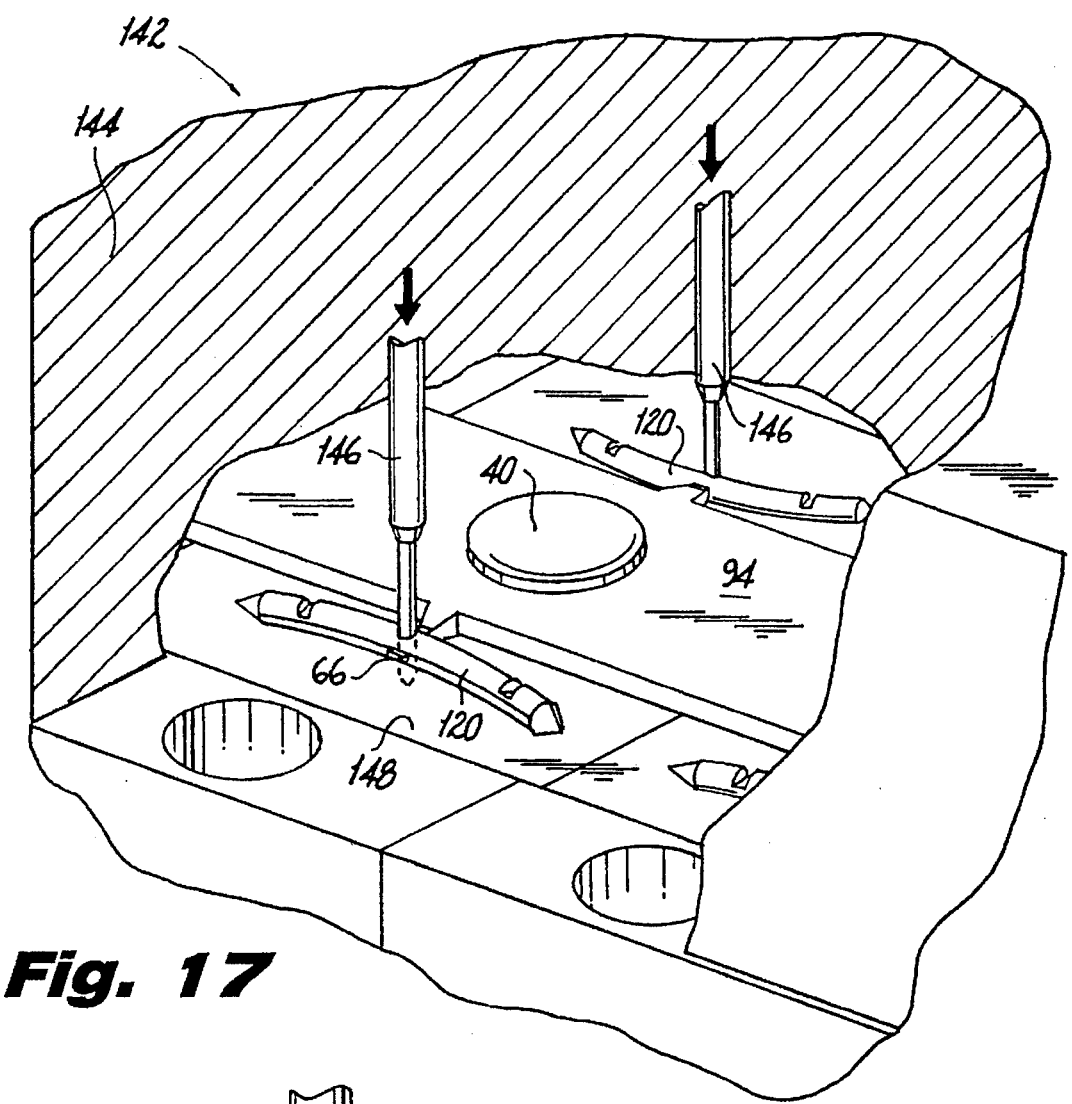
FIG. 17 is an enlarged perspective view of a suture attachment hole forming station forming suture attachment holes in opposed pairs of needle blanks.
Figure 18:
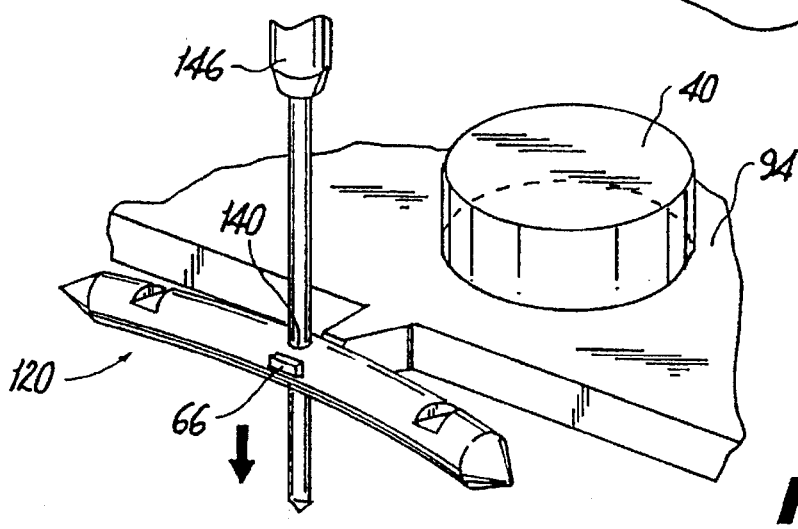
FIG. 18 is an enlarged perspective view of a portion of FIG. 17.

Referring now to FIGS. 17 and 18, there is disclosed a hole forming die station 142 which is configured to cream a hole through surgical needle 120 connecting dimples 140 and adjacent crimping bulge 66. As shown, hole forming die station 142 includes an upper die 144 having an opposed pair of hole forming members 146, for simultaneously engaging each needle 120 of the opposed pair, and a lower die 148. Preferably, hole forming members 146 are of the electrode type used in electronic discharge machines which will burn or melt a hole through surgical needles 120 without deformation. Impacting the needles 120 with a conventional die punch is also contemplated. While not shown, apparatus 10 may preferably be provided with an oil or other fluid flushing mechanism to cool the needles and die stations and to wash debris out of apparatus 10 during the various processing operations. It is also contemplated that the hole could be formed with the needle oriented with the notches facing away from the hole forming apparatus.

Figure 19:
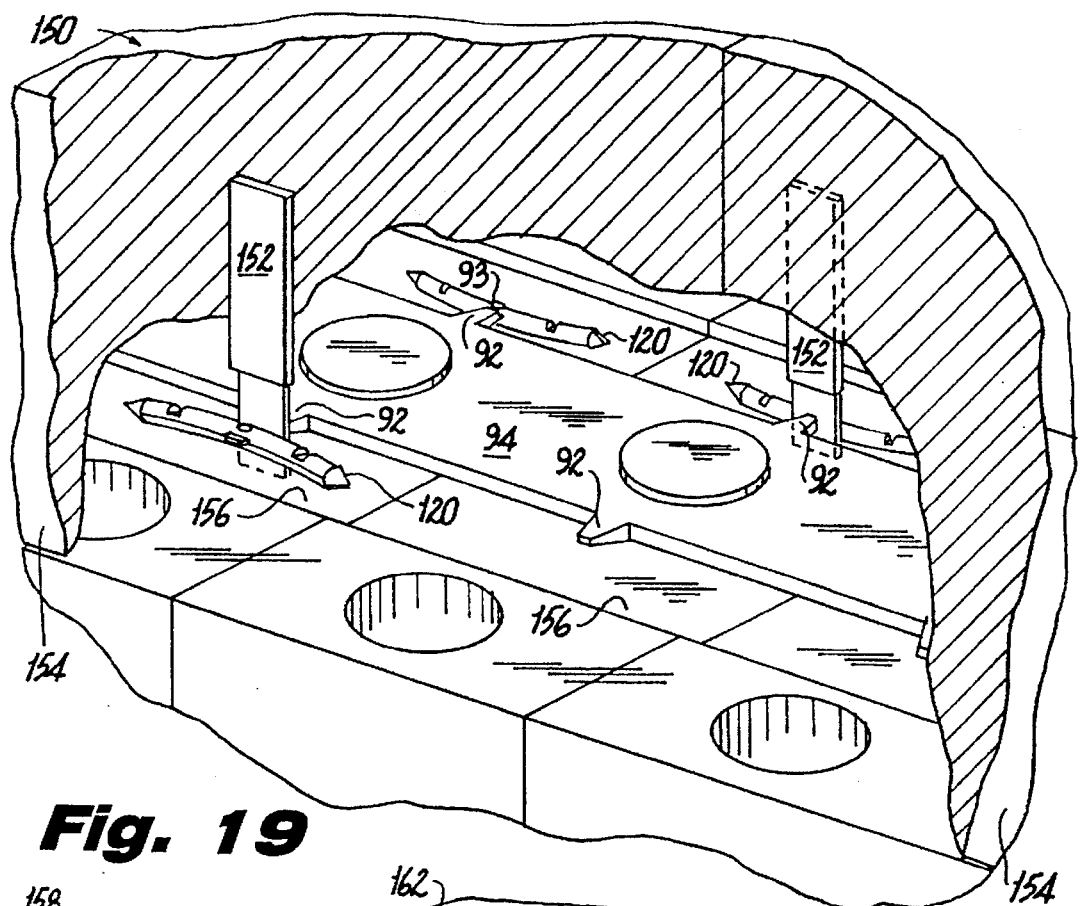
FIG. 19 illustrates a first embodiment of a severing station alternately severing each needle blank in an opposed pair of needle blanks.

Referring now to FIG. 19, there is disclosed a preferred embodiment of a needle severing station 150. Preferably, needle severing station 150 includes blade members 152 formed in upper dies 154 and which are configured to impact and sever reduced area portion 93 from leg 92. A lower die 156 is also provided to support needle 120. As shown in the preferred embodiment, the two die stations 150 are staggered and configured so as to each individually sever a single needle 120 from the opposed pair of needles at a time. Once severed, needles or surgical incision members 120 may be transported off apparatus 10 by a fluid or other means and collected in a suitable container.

Figure 20:
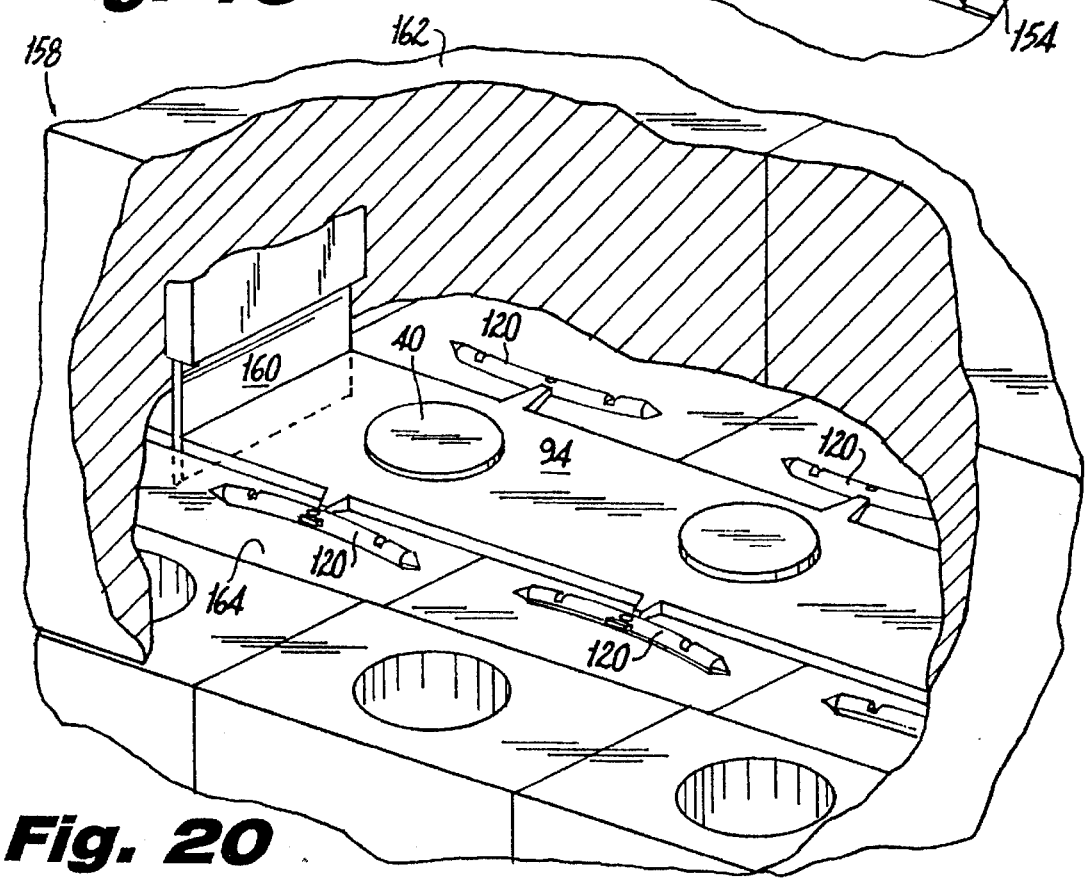
FIG. 20 is a second alternate embodiment of a severing station severing the carrier strip containing a plurality of opposed pairs of needle blanks.
Figure 21:
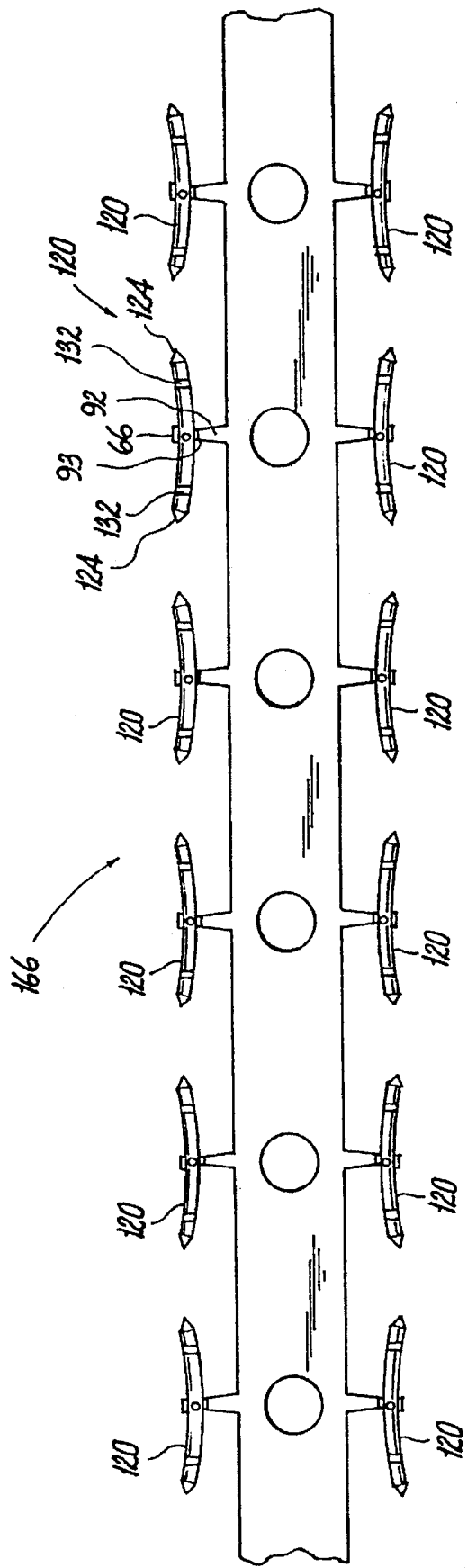
FIG. 21 is a top plan view of a carrier ship having a plurality of opposed pairs of needle blanks attached thereto as severed by the embodiment of FIG. 20.

Alternatively, referring for the moment to FIG. 20, there is disclosed an alternate method of removing the surgical needles from apparatus 10. Specifically, it may be desirable to initially remove a section of carrier strip 94 retaining the finished surgical needles 120 from apparatus 10. Thus, there is provided a carrier strip severing station 158 having a blade 160 affixed to an upper die 162. Upper blade 160 is configured to sever carrying strip 94 at a predetermined point along its length. Lower die 164 supports strip 94 during severing. In this manner apparatus 10 can be configured to provide a strip 166 consisting of carrier strip 94 with a plurality of attached surgical needles or incision members 120 as illustrated in FIG. 21.

As noted hereinabove, surgical needles 120 may be severed within apparatus 10 at severing station 150 or severed after strip 166 has been removed from apparatus 10.

Figure 22:
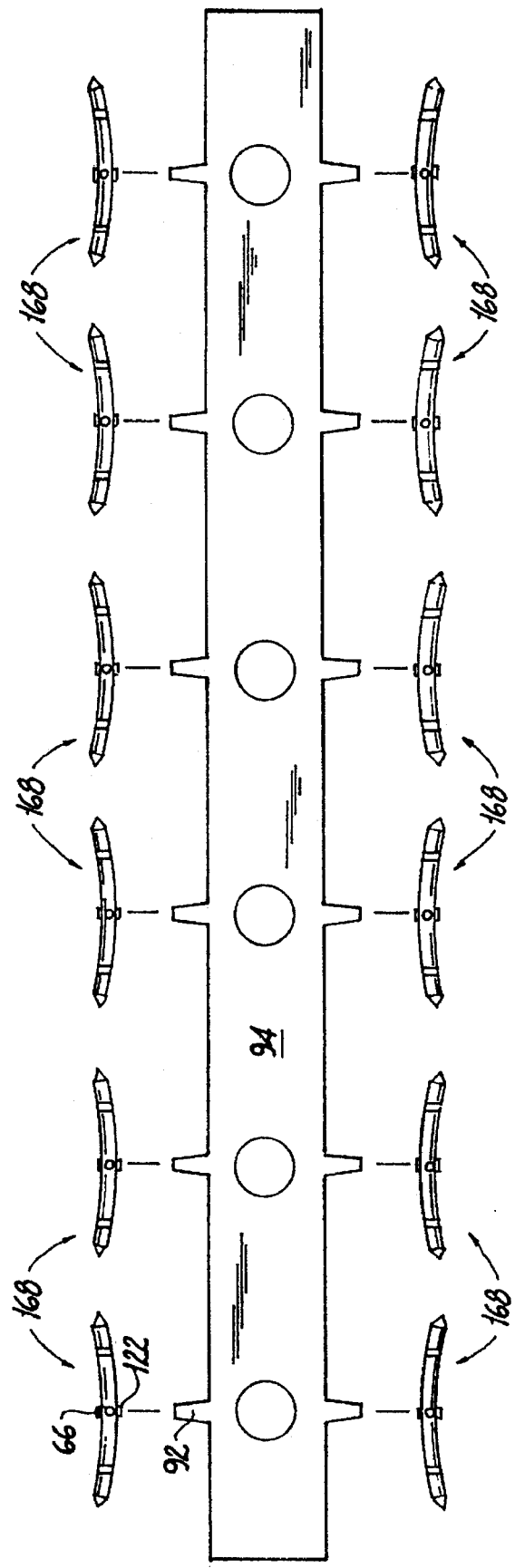
FIG. 22 is a top plan view of severed opposed pairs of needle blanks and carrier strip as severed from the embodiment of FIG. 19.

Referring to FIG. 22, there is disclosed a plurality of surgical needles or, more particularly, surgical incision members 168 severed from carrier strip 94.

Figure 24:
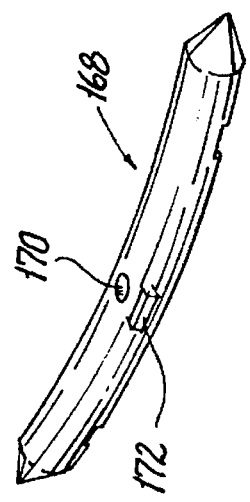
FIG. 24 is another perspective view of the surgical incision member formed on the apparatus of FIG. 1.
Figure 23:
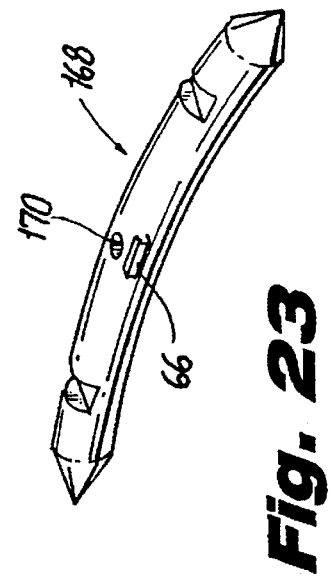
FIG. 23 is a perspective view a surgical incision member formed from the apparatus of FIG. 1.

An individual high strength surgical incision member is illustrated in FIGS. 23 and 24. Once severed from carrier strip 94, the reduced area portion 93 of leg 92 forms an additional crimping bulge 172 diametrically opposite crimping bulge 66. Once surgical incision members 168 have been severed from carrier strip 94 they may be taken to additional processing apparatus for tumbling and polishing in various media. Further, the needles may be passivated to remove any remaining grit and oils formed thereon. Additionally, sutures may be inserted through holes 170 and secured thereby by compressing crimping bulges 66 and 172 radially inwardly.

The disclosed surgical incision members formed herein have been found, through laboratory testing, to have a significantly higher bend strength than those formed from wire needle stock material or by the MIM process. For example, the tested bend moment of the disclosed surgical needles or incision members is greater than about 1,500 KPSI, and is on the order of approximately 1,650 KPSI, whereas the MIM and wire needles are on the order of approximately 1,000 KPSI or less. Further, the disclosed surgical needles retain an average ductility of about 323 degrees, while the MIM needles are about 79 degrees, and the wire formed needles are about 136 degrees when tested by bending the needle or surgical incision member back and forth through a series of ninety degree bends, and reported as the cumulative total degrees of bending prior to failure. Apparatus for testing the bending characteristics of needles are described in U.S. Pat. Nos. 5,022,273 and 5,297,440.

It will be understood that various modifications may be made to the embodiments disclosed herein. For example, various numbers and combinations of processing stations and dies may be provided and/or substituted as well as stations performing different functions, for example, imparting cutting edges to the needles, providing suture attachment structure at an end of the needle, etc.

Therefore, the above description should not be construed as limiting, but merely as exemplifications of preferred

What is claimed is:

1. An apparatus for forming solid body surgical needles from needle stock material comprising:
   a) a first processing station having first dies, the first dies configured and dimensioned to remove material from needle stock material to rough form a needle blank having first and second longitudinal ends and attached to the needle stock material intermediate the first and second longitudinal ends;
   b) a second processing station adjacent the first processing station and having second dies, the second dies configured and dimensioned to impact an outer surface of the needle blank to form a surgical needle attached to the remainder of needle stock material; and
   c) a separator engageable with the needle stock material to detach the needle therefrom.

2. The apparatus according to claim 1, wherein the first processing station removes material from the needle stock material to rough form an outer edge of the needle blank and a pair of inner edges of the needle blank separated by a leg connected to the needle stock material.

3. The apparatus according to claim 2, wherein, the second processing station imparts a predetermined body cross-section to the needle.

4. The progressive die apparatus according to claim 3, wherein the imparted body cross-section is substantially circular.

5. The apparatus according to claim 2, wherein the second processing station is further configured and dimensioned to impart predetermined shapes to ends of the needle.

6. The apparatus according to claim 5, wherein the predetermined shapes imparted to ends of the needle are substantially conical.

7. The apparatus according to claim 2, wherein the second processing station further includes dies configured and dimensioned to impart apparatus engagement structure into the needle.

8. The apparatus according to claim 7 wherein the second processing station further includes dies configured and dimensioned to impart at least one dimple to the needle.

9. The apparatus according to claim 8 wherein a dimple is imparted to opposite sides of the needle.

10. The apparatus according to claim 9, wherein the dies of the first and second processing stations simultaneously engage the needle stock material.

11. The apparatus according to claim 1, wherein the first and second processing stations form an opposed pair of needles separated by the needle stock material.

12. An apparatus for forming solid body surgical needles from needle stock material comprising:
    a) a first processing station having first dies, the first dies configured and dimensioned to remove material from needle stock material to form an opposed pair of needles attached to the needle stock material at respective leg portions, the leg portions being intermediate opposite ends of each needle of the opposed pair of needles; and
    b) a separator engageable with the leg portions to detach the needles from the needle stock material.

13. A method of forming a solid body surgical needle comprising the steps of:
    a) providing needle stock material;
    b) removing material from the needle stock material to rough form a needle blank attached to the remainder of the needle stock material at a point centrally located with respect to opposed ends of the needle blank;
    c) coining the needle blank to impart a predetermined outer surface profile to the needle blank to form a needle; and
    d) separating the needle from the needle stock material.

14. The method according to claim 13, wherein the step of providing includes the step of providing a length of flat needle stock material.

15. The method according to claim 14, wherein the step of removing material includes the step of forming an inner edge of the needle blank and a pair of outer edges of the needle blank separated by a leg attached to the needle stock material.

16. The method according to claim 15, wherein the inner and outer edges of the needle blank define a radius of curvature of the needle blank.

17. The method according to claim 13, wherein the step of removing includes the step of forming a pre-point on an at least one end of the needle blank.

18. The method according to claim 13, wherein the step of coining includes the step of imparting a predetermined cross-section to the needle.

19. The method according to claim 14, wherein the predetermined cross-section is substantially circular.

20. The method according to claim 14, wherein the step of coining includes the step of forming a substantially conical point on at least one end of the needle blank.

21. The method according to claim 14, wherein the coining step includes the step of forming apparatus engagement structure in the needle blank.

22. The method according to claim 14, wherein the coining step includes the step of forming pilot holes in the needle.

23. The method according to claim 17, further comprising forming a suture hole through the pilot hole.

24. The method according to claim 14, further comprising the stop of rough simultaneously forming an opposed pair of needle blanks attached to the carrier strip.

* * * * *